United States Patent
Robert et al.

(10) Patent No.: US 8,952,179 B2
(45) Date of Patent: Feb. 10, 2015

(54) SYNTHESIS PROCESS, AND CRYSTALLINE FORM OF 4-{3-[CIS-HEXAHYDROCYCLOPENTA[C]PYRROL-2(1H)-YL]PROPOXY} BENZAMIDE HYDROCHLORIDE AND PHARMACEUTICAL COMPOSITIONS CONTAINING IT

(71) Applicant: Les Laboratoires Servier, Suresnes Cedex (FR)

(72) Inventors: Nicolas Robert, Le Havre (FR); Jean-Michel Lerestif, Yvetot (FR); Jean-Pierre Lecouve, Le Havre (FR); Marina Gaillard, Orleans (FR); Loïc Meunier, Vennecy (FR); Philippe Letellier, Orleans (FR); Mathieu Boiret, Orleans (FR)

(73) Assignee: Les Laboratories Servier, Suresnes Cedex (FR)

( * ) Notice: Subject to any disclaimer, the term of this patent is extended or adjusted under 35 U.S.C. 154(b) by 0 days.

(21) Appl. No.: 14/103,006

(22) Filed: Dec. 11, 2013

(65) Prior Publication Data

US 2014/0100374 A1 Apr. 10, 2014

Related U.S. Application Data

(62) Division of application No. 13/489,691, filed on Jun. 6, 2012, now Pat. No. 8,664,408.

(30) Foreign Application Priority Data

Jun. 8, 2011 (FR) ...................... 11 01746

(51) Int. Cl.
| | | |
|---|---|---|
| C07D 209/52 | (2006.01) | |
| C07C 309/63 | (2006.01) | |
| C07C 235/46 | (2006.01) | |
| C07D 317/22 | (2006.01) | |
| C07D 319/06 | (2006.01) | |

(52) U.S. Cl.
CPC ............. *C07C 309/63* (2013.01); *C07C 235/46* (2013.01); *C07D 209/52* (2013.01); *C07D 317/22* (2013.01); *C07D 319/06* (2013.01); *C07B 2200/13* (2013.01)
USPC ............ 548/515; 564/183; 549/373; 549/451

(58) Field of Classification Search
CPC combination set(s) only.
See application file for complete search history.

(56) References Cited

U.S. PATENT DOCUMENTS 7,576,120 B2 * 8/2009 Casara et al. ................. 514/412

FOREIGN PATENT DOCUMENTS

| WO | WO2005/089747 | 9/2005 |
|---|---|---|
| WO | WO2010/043787 | 4/2010 |
| WO | WO2011/070251 | 6/2011 |

OTHER PUBLICATIONS

French Preliminary Search Report for FR11/01746 of Dec. 19, 2011.
G. Roussi J. Zhang, Tetrahedron Letters, vol. 29, No. 28, p. 3481-3482, 1988.
Passani et al. Neuroscience and Biobehavioral Reviews 24 (2000) 107-113.

* cited by examiner

*Primary Examiner* — Nyeemah A Grazier
(74) *Attorney, Agent, or Firm* — Hueschen and Sage

(57) ABSTRACT

Industrial synthesis process for the compound of formula (I):

(I)

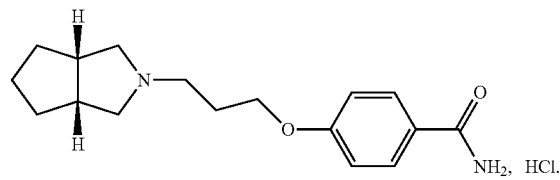

16 Claims, No Drawings

SYNTHESIS PROCESS, AND CRYSTALLINE FORM OF 4-{3-[CIS-HEXAHYDROCYCLOPENTA[C]PYRROL-2(1H)-YL]PROPOXY} BENZAMIDE HYDROCHLORIDE AND PHARMACEUTICAL COMPOSITIONS CONTAINING IT

The present invention relates to a process for the industrial synthesis of 4-{3-[cis-hexahydrocyclopenta[c]pyrrol-2(1H)-yl]propoxy}benzamide hydrochloride of formula (I):

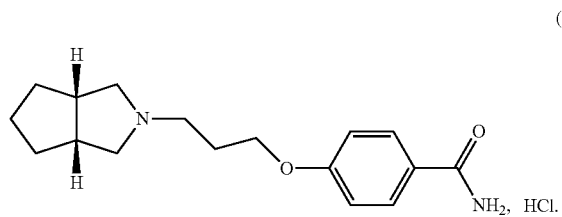

The present invention relates also to crystalline form I of 4-{3-[cis-hexahydrocyclopenta[c]pyrrol-2(1H)-yl]propoxy}benzamide hydrochloride, to a process for its preparation and also to pharmaceutical compositions containing it.

Crystalline form I of the free base of the compound of formula (I) is, moreover, also obtained by the process of the invention and forms an integral part of the invention, as do pharmaceutical compositions containing it.

4-{3-[cis-Hexahydrocyclopenta[c]pyrrol-2(1H)-yl]propoxy}benzamide has the characteristic of interacting with central histaminergic systems in vivo. These properties provide it with activity in the central nervous system and, more especially, in the treatment of cognitive deficiencies associated with cerebral aging and with neurodegenerative diseases.

4-{3-[cis-Hexahydrocyclopenta[c]pyrrol-2(1H)-yl]propoxy}benzamide, its preparation in the form of an oxalate and its therapeutic use have been described in Patent Application WO2005/089747.

In view of the pharmaceutical value of this compound it was important to be able to obtain it by an effective synthesis process that is readily transferable to the industrial scale, yielding 4-{3-[cis-hexahydrocyclopenta[c]pyrrol-2(1H)-yl]propoxy}benzamide hydrochloride in a good yield and with excellent purity.

It was also important to be able to obtain 4-{3-[cis-hexahydrocyclopenta[c]pyrrol-2(1H)-yl]propoxy}benzamide hydrochloride in a well-defined, perfectly reproducible crystalline form having valuable filtration characteristics and ease of formulation.

The Patent Application WO2005/089747 describes obtaining 4-{3-[cis-hexahydrocyclopenta[c]pyrrol-2(1H)-yl]propoxy}benzamide oxalate in three steps starting from 4-hydroxybenzonitrile, which undergoes an O-alkylation reaction before being coupled to an octahydrocyclopenta[c]pyrrole-type ring system to form 4-{3-[cis-hexahydrocyclopenta[c]pyrrol-2(1H)-yl]propoxy}benzonitrile. The latter compound is finally subjected to basic hydrolysis in order to yield 4-{3-[cis-hexahydrocyclopenta[c]pyrrol-2(1H)-yl]propoxy}benzamide, which is crystallised in the form of an oxalate. The yield for these three steps is 46.6%.

The present invention relates to a new industrial synthesis process which yields 4-{3-[cis-hexahydrocyclopenta[c]pyrrol-2(1H)-yl]propoxy}benzamide hydrochloride with satisfactory purity from the pharmaceutical point of view and in an effective yield from the industrial point of view. By virtue of this process it is possible to ensure a very low level of genotoxic impurities, which is compatible with regulatory requirements.

The present invention relates, more specifically, to a process for the industrial synthesis of the compound of formula (I):

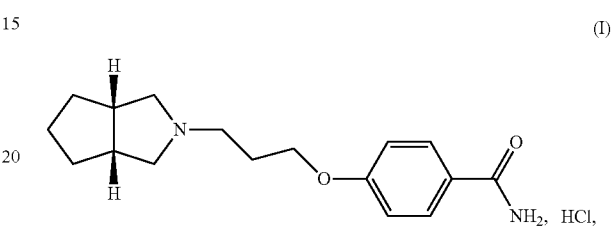

which process is characterised in that the compound of formula (II):

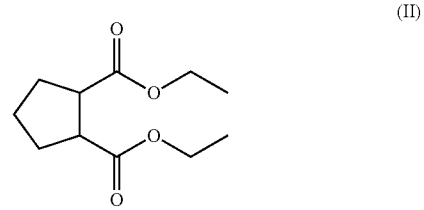

is reacted with ammonia at a temperature greater than 100° C. to form the compound of formula (III):

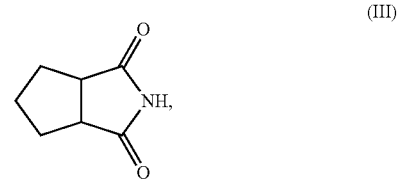

which is reduced to yield the bicyclic amine of formula (IV):

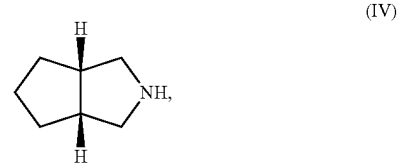

which latter compound is subsequently subjected:
either to a coupling reaction, under basic conditions in a polar medium, with a compound of formula (V):

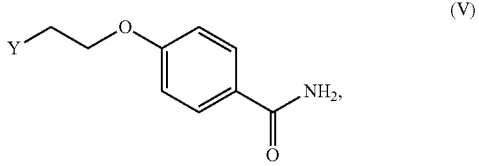

wherein Y represents —CH$_2$-Hal wherein Hal is a halogen, or a group —CH$_2$—OSO$_2$—R wherein R is a (C$_1$-C$_6$)alkyl group or a —C$_6$H$_4$—CH$_3$ group,
or to reductive amination, in an acid medium, with a compound of formula (V'):

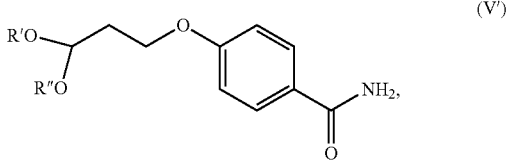

wherein R' and R" represent, each independently of the other, a (C$_1$-C$_6$)alkyl group, or R' and R" together form a group —(CH$_2$)$_n$— wherein n=2-3, or one of the groups R' and R" represents a hydrogen atom and the other represents a (C$_1$-C$_6$)alkyl group,
or to reductive amination with the compound of formula (V"):

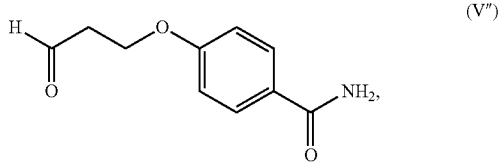 [SMILES: NC(=O)c1ccc(OCCC=O)cc1]

to yield the free base of the compound of formula (I), which is placed in the presence of HCl to form the compound of formula (I), which is isolated in the form of a solid.

In a preferred embodiment of the invention, the reaction mixture obtained at the end of the reaction of the compound of formula (II) with ammonia is subjected to pyrolysis. The pyrolysis in question is carried out preferably at a temperature greater than or equal to 200° C., and even more preferably at a temperature greater than or equal to 280° C.

Conversion of the compound of formula (III) into the compound of formula (IV) is advantageously carried out in the presence of hydrogen and a metal or metal-containing catalyst.

Preference is given to the compound of formula (V) being 4-(3-chloropropoxy)benzamide.

The coupling reaction of the compound of formula (IV) with the compound of formula (V) is preferably carried out in the presence of a carbonate, an amine or a hydroxide. Among the preferred carbonates, amines and hydroxides there may be mentioned potassium carbonate, caesium carbonate, triethylamine, pyridine, potassium hydroxide, sodium hydroxide and lithium hydroxide. Even more preferably, the coupling reaction of the compound of formula (IV) with the compound of formula (V) is carried out in the presence of potassium carbonate or triethylamine. This reaction is moreover advantageously performed in a polar medium composed of one or more polar solvents selected from water, alcohols, ketones, ethers, amides, DMSO and acetonitrile. Preferred alcohols are methanol, ethanol, isopropanol and butanol. The preferred solvents also include acetone and methyl ethyl ketone among the ketones, tetrahydrofuran, methyltetrahydrofuran and cyclopentyl methyl ether among the ethers, and also N-methyl-2-pyrrolidone among the amides. Even more preferably, the coupling reaction of the compound of formula (IV) with the compound of formula (V) is performed in a water/acetonitrile mixture or a water/isopropanol mixture.

In the case of reductive amination, in an acid medium, of the compound of formula (IV) with a compound of formula (V'), the latter is preferably 4-(3,3-diéthoxypropoxy)benzamide.

Furthermore, the step of forming a salt from the free base of the compound of formula (I) in the presence of HCl preferably takes place in a solvent selected from water, acetone and an alcohol. Preferred alcohols are methanol, ethanol and isopropanol. Acetone and isopropanol are more especially preferred for this salt formation step.

Optionally, the compound of formula (I) isolated at the end of the salt formation step is subjected to recrystallisation.

It is important to emphasise that this synthesis process makes it possible to obtain the compound 4-{3-[cis-hexahydrocyclopenta[c]pyrrol-2(1H)-yl]propoxy}benzamide, exclusively, in a satisfactory yield on the industrial scale, and not its trans homologue. Besides this advantage, it makes it possible to keep the levels of genotoxic impurities (especially 4-(3-chloropropoxy)benzamide) present in the batches well below the regulatory threshold.

The compounds of formula (V) wherein Y represents a group —CH$_2$—OSO$_2$—R wherein R is a (C$_1$-C$_6$)alkyl group or a —C$_6$H$_4$—CH$_3$ group and the compounds of formula (V') are new and useful as intermediates in the synthesis of compound of formula (I). The compound of formula (V") is also useful as intermediate in the synthesis of compound of formula (I).

The invention relates also to crystalline form I of 4-{3-[cis-hexahydrocyclopenta[c]pyrrol-2(1H)-yl]propoxy}benzamide hydrochloride obtained according to the process described above. This crystalline form is well-defined, perfectly reproducible and consequently has valuable characteristics of filtration, drying, stability and ease of formulation.

Crystalline form I of the compound of formula (I) is characterised by an X-ray powder diffraction diagram having the following diffraction lines (Bragg's angle 2 theta, expressed in degrees ±0.2°): 16.97°, 17.84°, 18.90°, 20.32°, 23.87°, 27.10°, 27.86° and 30.34°.

More specifically, crystalline form I of 4-{3-[cis-hexahydrocyclopenta[c]pyrrol-2(1H)-yl]propoxy}benzamide hydrochloride is characterised further by the X-ray powder diffraction diagram below, measured using a PANalytical X'Pert Pro MPD diffractometer with an X'Celerator detector, and expressed in terms of line position (Bragg's angle 2 theta, expressed in degrees ±0.2°) and interplanar distance d (expressed in Å):

| Line no. | Angle 2-theta (degrees) | Interplanar distance (Å) |
|---|---|---|
| 1 | 16.97 | 5.219 |
| 2 | 17.84 | 4.967 |
| 3 | 18.90 | 4.690 |
| 4 | 20.32 | 4.366 |
| 5 | 23.87 | 3.724 |

-continued

| Line no. | Angle 2-theta (degrees) | Interplanar distance (Å) |
|---|---|---|
| 6 | 27.10 | 3.288 |
| 7 | 27.86 | 3.200 |
| 8 | 30.34 | 2.943 |

Besides that, form I of 4-{3-[cis-hexahydrocyclopenta[c]pyrrol-2(1H)-yl]propoxy}benzamide hydrochloride has been characterised by Raman spectroscopy. Significant peaks were observed in the following locations: 1676 cm$^{-1}$, 1606 cm$^{-1}$, 1564 cm$^{-1}$, 1152 cm$^{-1}$, 830 cm$^{-1}$ and 296 cm$^{-1}$.

Alternatively, form I of 4-{3-[cis-hexahydrocyclopenta[c]pyrrol-2(1H)-yl]propoxy}benzamide hydrochloride may be characterised by the X-ray powder diffraction diagram having the 8 significant lines given above and also by a Raman spectrum having a significant peak at the location 1606 cm$^{-1}$ or 1676 cm$^{-1}$.

Obtaining this crystalline form has the advantage of allowing especially rapid and efficient filtration and also the preparation of pharmaceutical formulations having a consistent and reproducible composition, which is especially advantageous when those formulations are intended for oral administration. Furthermore, form I of 4-{3-[cis-hexahydrocyclopenta[c]pyrrol-2(1H)-yl]propoxy}benzamide hydrochloride has noteworthy properties of immediate dissolution.

The form thereby obtained is sufficiently stable to allow its storage for an extended period without particular conditions for temperature, light, humidity or oxygen levels. More specifically, form I of 4-{3-[cis-hexahydrocyclopenta[c]pyrrol-2(1H)-yl]propoxy}benzamide hydrochloride has been found to be very stable over periods of up to 18 months under the following conditions:

- at 25° C. with a humidity level of 60% in a double bag of polyethylene,
- at 30° C. with a humidity level of 65% in a double bag of polyethylene,
- at 30° C. with a humidity level of 85% in a double bag of polyethylene.

Another aspect of the invention relates to crystalline form I of the free base of 4-{3-[cis-hexahydrocyclopenta[c]pyrrol-2(1H)-yl]propoxy}benzamide obtained according to the process described above. This crystalline form is well-defined and perfectly reproducible. Obtaining this form and isolating it in the course of the synthesis process for the hydrochloride of formula (I) described above make it possible to eliminate a large proportion of the genotoxic impurities present in the batches.

Crystalline form I of the free base of the compound of formula (I) is characterised by its X-ray powder diffraction diagram having the following diffraction lines (Bragg's angle 2 theta, expressed in degrees ±0.2°): 6.25°, 12.55°, 17.74°, 18.19°, 19.43°, 20.72°, 21.00°, 23.50° and 27.00°.

More specifically, crystalline form I of the free base of 4-{3-[cis-hexahydrocyclopenta[c]pyrrol-2(1H)-yl]propoxy}benzamide is characterised further by the X-ray powder diffraction diagram below, measured using a PANalytical X'Pert Pro MPD diffractometer with an X'Celerator detector, and expressed in terms of line position (Bragg's angle 2 theta, expressed in degrees ±0.2°) and interplanar distance d (expressed in Å):

| Line no. | Angle 2-theta (degrees) | Interplanar distance (Å) |
|---|---|---|
| 1 | 6.25 | 14.131 |
| 2 | 12.55 | 7.049 |
| 3 | 17.74 | 4.997 |
| 4 | 18.19 | 4.873 |
| 5 | 19.43 | 4.565 |
| 6 | 20.72 | 4.284 |
| 7 | 21.00 | 4.226 |
| 8 | 23.50 | 3.782 |
| 9 | 27.00 | 3.297 |

In addition, form I of the free base of 4-{3-[cis-hexahydrocyclopenta[c]pyrrol-2(1H)-yl]propoxy}benzamide has been characterised by Raman spectroscopy. Significant peaks were observed in the following locations: 292 cm$^{-1}$, 618 cm$^{-1}$, 1045 cm$^{-1}$, 1483 cm$^{-1}$, 1568 cm$^{-1}$, 1683 cm$^{-1}$.

Alternatively, form I of the free base of 4-{3-[cis-hexahydrocyclopenta[c]pyrrol-2(1H)-yl]propoxy}benzamide may be characterised by the X-ray powder diffraction diagram having the 9 significant lines given above and also by a Raman spectrum having a significant peak at the location 1683 cm$^{-1}$.

Finally, form I of the free base of 4-{3-[cis-hexahydrocyclopenta[c]pyrrol-2(1H)-yl]propoxy}benzamide has also been characterised by solid-state NMR spectroscopy. Significant peaks were observed at 112.2 ppm, 119.2 ppm, 127.2 ppm, 128.6 ppm, 132.4 ppm, 162.2 ppm and 173.2 ppm. More precisely, the $^{13}$C CP/MAS (Cross Polarization Magic Angle Spinning) spectra have the following peaks (expressed in ppm±0.2 ppm):

| Peak no. | Chemical shift (ppm) |
|---|---|
| 1 | 173.2 |
| 2 | 162.2 |
| 3 | 132.4 |
| 4 | 128.6 |
| 5 | 127.2 |
| 6 | 119.2 |
| 7 | 112.2 |
| 8 | 67.1 |
| 9 | 64.0 |
| 10 | 59.7 |
| 11 | 52.1 |
| 12 | 44.5 |
| 13 | 42.8 |
| 14 | 31.5 |
| 15 | 30.8 |
| 16 | 30.2 |
| 17 | 26.2 |

Pharmacological study of form I of 4-{3-[cis-hexahydrocyclopenta[c]pyrrol-2(1H)-yl]propoxy}benzamide hydrochloride and also that of form I of its free base have shown substantial activity on the central nervous system which makes it possible to establish its usefulness in the treatment of cognitive and psycho-behavioural disorders associated with cerebral aging and with neurodegenerative diseases, and also in the treatment of mood disorders, attention-deficit hyperactivity syndrome, obesity and pain. Neurodegenerative diseases more especially targeted are Alzheimer's disease, Parkinson's disease, Pick's disease, Korsakoff's disease, Lewy body dementias, frontal and subcortical dementias, frontotemporal dementias and vascular dementias.

The invention relates also to pharmaceutical compositions comprising as active ingredient crystalline form I of 4-{3-[cis-hexahydrocyclopenta[c]pyrrol-2(1H)-yl]propoxy}benzamide hydrochloride, or crystalline form I of its free base, together with one or more appropriate, non-toxic, inert excipients. Among the pharmaceutical compositions according to the invention there may be more especially mentioned those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The useful dosage can be varied according to the nature and severity of the disorder, the administration route and also the age and weight of the patient. The useful dosage varies from 1 mg to 100 mg per day, in one or more administrations. Preferably, crystalline form I of 4-{3-[cis-hexahydrocyclopenta[c]pyrrol-2(1H)-yl]propoxy}benzamide hydrochloride is administered at daily doses (expressed as free base equivalent) of 2 mg, 5 mg and 20 mg (or, that is to say, 2.25 mg, 5.63 mg and 22.52 mg of the hydrochloride).

The Examples hereinbelow illustrate the invention.

Preparation 1: 4-(3-Chloropropoxy)benzamide 10.5 kg of 4-hydroxybenzamide, 10.58 kg of potassium carbonate and 83 kg of acetonitrile are introduced into a reactor. The mixture is stirred and then there are added 24.14 kg of a solution of 1-bromo-3-chloropropane. The reaction mixture is heated at reflux for 4 hours. Water (105 L) is added in the hot state, the mixture is then cooled to 5° C. and filtered. The filter cake is washed with water and then with acetonitrile. The title product is obtained in the form of a powder in a yield of 82%.

Melting point: 144° C.

Preparation 2: 4-(3-Oxopropoxy)benzamide

Step A: 4-(3,3-Diethoxypropoxy)benzamide 500 mg of 4-hydroxybenzamide, 1.51 g of potassium carbonate, 10 mL of DMF and 730 mg of 3-chloro-1,1-diethoxypropane are added to a flask. The reaction mixture is stirred at 100° C. for 18 hours and then 5 mL of water are added. The aqueous phase is extracted with ethyl acetate, and then the organic phases are collected, washed with water and concentrated under reduced pressure. The product is obtained in the form of a powder in a yield of 89% and with a chemical purity of 95%.

Melting point: 108° C.

Step B: 4-(3-Oxopropoxy)benzamide 5 g of the product obtained in Step A, 100 ml of THF and 94 mL of 1N hydrochloric acid solution are added to a flask. The mixture is stirred at ambient temperature for 1 hour. The aqueous phase is extracted with dichloromethane, and then the organic phases are concentrated under reduced pressure. The product is obtained in the form of a solid in a yield of 96% and with a chemical purity of 93%.

Example 1

4-{3-[cis-Hexahydrocyclopenta[c]pyrrol-2(1H)-yl]propoxy}benzamide hydrochloride

Step A:
Tetrahydrocyclopenta[c]pyrrole-1,3(2H,3aH)-dione

Load 1 kg of diethyl 1,2-cyclopentanedicarboxylate and 1.02 kg of 27% ammonia into an autoclave. The reaction mixture is heated in the autoclave at a temperature of 130° C. for a minimum of 4 hours. After cooling to 60° C. and depressurisation, evaporation of the solvent is carried out. The residue is then subjected to pyrolysis at 280° C. for 1 hour. The imide is purified by distillation in vacuo (4-12 mbars) at a temperature of 200° C. After isolation, the title product is obtained in a yield of 96%.

Melting point: 89° C.

Step B: cis-Octahydrocyclopenta[c]pyrrole 1 kg of the imide of Step A, 250 g of copper chromite and 2 L of dioxane are loaded into a reactor. The reaction mixture is stirred at a temperature of 265° C. and under a hydrogen pressure of 205 bars until the absorption of hydrogen is complete. After cooling of the reactor, the catalyst is filtered off.

The hydrogenation liquors are loaded into a separator and then 0.37 L of water is added. The pH is adjusted to a pH of less than 3 by adding sulphuric acid 96%. The lower, aqueous phase is drawn off. After adding 2.5 L of water, the residual dioxane is removed by azeotropic distillation with monitoring of the refractive index. The pH is then brought to 13 by adding 30% sodium hydroxide solution. The title product is purified by azeotropic distillation with water to obtain a 30% solution by weight in a yield of 83%.

Step C: 4-{3-[cis-Hexahydrocyclopenta[c]pyrrol-2(1H)-yl]propoxy}benzamide 13.35 kg of 4-(3-chloropropoxy)benzamide obtained according to Preparation 1, 10.33 kg of potassium carbonate and 168 kg of acetonitrile are introduced into a reactor. The mixture is stirred. There are then loaded 34.74 kg of cis-octahydrocyclopenta[c]pyrrole in a 30% aqueous solution, 26.7 L of water. The reaction mixture is heated at reflux until all the starting material has been consumed. Then water (13.3 L) is added. The mixture is cooled to 5° C., before being filtered and washed with water. The title product is obtained in the form of a solid in a yield of 81% and with a chemical purity of 96%.

$^1$H NMR: δ (600.13 MHz; DMSO-d6; 300K): 7.82 (d, 2H, J=9.0 Hz); 7.79 (bs, 1H); 7.14 (bs, 1H); 6.95 (d, 2H, J=9.0 Hz); 4.06 (t, 2H, J=6.5 Hz); 2.57 (m, 2H); 2.48 (m, 2H); 2.44 (bt, 2H, J=6.5 Hz); 2.14 (bd, 2H, J=7.5 Hz); 1.86 (qt, 2H, J=6.5 Hz); 1.65-1.55 (m, 3H); 1.45-1.38 (m, 1H); 1.37-1.30 (m, 2H)

where bs: broad singlet; bd: broad doublet; bt: broad triplet

Characterisation of the product thereby formed, using the techniques given in Examples 6 to 8, demonstrated that the crystalline form I of the free base was obtained.

Step D: 4-{3-[cis-Hexahydrocyclopenta[c]pyrrol-2(1H)-yl]propoxy}benzamide hydrochloride 14.69 kg of 4-{3-[cis-hexahydrocyclopenta[c]pyrrol-2(1H)-yl]propoxy}benzamide and 122 L of water are introduced into a reactor. A solution of 6.81 kg of 37% hydrochloric acid in 11.54 L of water is also prepared. 13.75 kg of this acid solution are added to the reactor. The mixture is stirred for 1 hour at ambient temperature, and then for 1 hour 30 minutes at 60° C. The suspension is filtered in the hot state and the filter is then rinsed with water. A solvent change is then carried out on the filtrate, keeping the volume constant, in order to obtain an isopropanol/water ratio of 9/1. The product is isolated at 0° C. and the precipitate obtained is washed with isopropanol. The title product is finally obtained in a yield of 89% and with a chemical purity greater than 99%.

Characterisation of the product thereby formed, using the techniques given in Examples 4 to 5, demonstrated that the crystalline form I of the hydrochloride was obtained.

Step E: 4-{3-[cis-Hexahydrocyclopenta[c]pyrrol-2(1H)-yl]propoxy}benzamide hydrochloride The hydrochloride salt obtained in Step D is recrystallised from a mixture of isopropanol (264 kg) and water (37.4 L). The mixture is heated at reflux for 45 minutes. The solution is filtered in the hot state and then rinsed with isopropanol. Crystallisation is then initiated at 55° C. The mixture is maintained at that temperature for 40 minutes before being cooled to 0° C. After several hours, the product is isolated by filtration. After washing with isopropanol, the title product is obtained in the form of a powder in a yield of 93% and with a chemical purity greater than 99%.

Melting point: 213-215° C.

Characterisation of the product thereby formed, using the techniques given in Examples 4 to 5, demonstrated that the crystalline form I of the hydrochloride was obtained.

Example 2

4-{3-[cis-Hexahydrocyclopenta[c]pyrrol-2(1H)-yl]propoxy}benzamide hydrochloride

Step A:
Tetrahydrocyclopenta[c]pyrrole-1,3(2H,3aH)-dione

The procedure is the same as that described in Step A of Example 1.

Step B: cis-Octahydrocyclopenta[c]pyrrole

The procedure is the same as that described in Step B of Example 1.

Step C: 4-{3-[cis-Hexahydrocyclopenta[c]pyrrol-2(1H)-yl]propoxy}benzamide 15.2 kg of 4-(3-chloropropoxy)benzamide, 40.28 kg of cis-octahydrocyclopenta[c]pyrrole in 30% aqueous solution, 63.84 kg of water, 21.48 kg of isopropanol and 14.39 kg of triethylamine are introduced into a reactor. The reaction mixture is stirred and heated at reflux until all the starting material has been consumed. The reaction mixture is then cooled to 20° C., before being filtered and washed with a mixture of isopropanol and water. The product is obtained in the form of a powder in a yield of 83% and with a chemical purity of 97%.

$^1$H NMR: δ (600.13 MHz; DMSO-d6; 300K): 7.82 (d, 2H, J=9.0 Hz); 7.79 (bs, 1H); 7.14 (bs, 1H); 6.95 (d, 2H, J=9.0 Hz); 4.06 (t, 2H, J=6.5 Hz); 2.57 (m, 2H); 2.48 (m, 2H); 2.44 (bt, 2H, J=6.5 Hz); 2.14 (bd, 2H, J=7.5 Hz); 1.86 (qt, 2H, J=6.5 Hz); 1.65-1.55 (m, 3H); 1.45-1.38 (m, 1H); 1.37-1.30 (m, 2H)

where bs: broad singlet; bd: broad doublet; bt: broad triplet

Characterisation of the product thereby formed, using the techniques given in Examples 6 to 8, demonstrated that the crystalline form I of the free base was obtained.

Step D: 4-{3-[cis-Hexahydrocyclopenta[c]pyrrol-2(1H)-yl]propoxy}benzamide hydrochloride 16.49 kg of 4-{3-[cis-hexahydrocyclopenta[c]pyrrol-2(1H)-yl]propoxy}benzamide, 16.36 kg of acetone, 6.76 kg of concentrated aqueous hydrochloric acid and 18.96 kg of water are introduced into a reactor. The mixture is stirred and heated at 50° C. for 1 hour. The mixture is then filtered in the hot state into a second reactor containing 57.67 kg of acetone and 1.65 kg of water. The mixture is then brought to reflux and 73.32 kg of acetone are added. Reflux is maintained for 10 minutes and then cooling to 0° C. is carried out. The product is filtered off and the solid obtained is washed with acetone. The product is obtained in the form of a powder in a yield of 85% and with a chemical purity greater than 99%.

Characterisation of the product thereby formed, using the techniques given in Examples 4 to 5, demonstrated that the crystalline form I of the hydrochloride was obtained.

Example 3

4-{3-[cis-Hexahydrocyclopenta[c]pyrrol-2(1H)-yl]propoxy}benzamide hydrochloride

Step A:
Tetrahydrocyclopenta[c]pyrrole-1,3(2H,3aH)-dione

The procedure is the same as that described in Step A of Example 1.

Step B: cis-Octahydrocyclopenta[c]pyrrole

The procedure is the same as that described in Step B of Example 1.

Step C: cis-Octahydrocyclopenta[c]pyrrole hydrochloride 2 g of cis-octahydrocyclopenta[c]pyrrole are dissolved in 10 mL of ethanol in a flask. The solution is cooled to 0° C., and there are then added 1.64 mL of concentrated hydrochloric acid solution (11M). The reaction mixture is stirred at 20° C. for 30 minutes before being concentrated under reduced pressure. The reaction mixture is stirred in methyl tert-butyl ether at 0° C. The product is isolated by filtration in the form of a solid in a yield of 83% and with a chemical purity of 99%.

Melting point: 126° C.

Step D: 4-{3-[cis-hexahydrocyclopenta[c]pyrrol-2(1H)-yl]propoxy}benzamide hydrochloride 915 mg of the product obtained in Step C, 1.65 g of sodium triacetoxyborohydride, 45 mL of THF and 7.5 mL of trimethyl orthoformate are added into a reactor. There are then added 1 g of the compound obtained in Preparation 2. The reaction mixture is heated at 40° C. for 50 minutes and then cooled to ambient temperature. There are then added a saturated NaHCO$_3$ solution. The aqueous phase is extracted with ethyl acetate, and then the organic phases are combined and washed with water. The organic phase is dried over MgSO$_4$, filtered and concentrated under reduced pressure. The residue is suspended in an isopropanol/water mixture in the presence of hydrochloric acid. The reaction mixture is heated at 40° C. then cooled to 5° C. The product is isolated by filtration in the form of a solid in a yield of 33% and with a chemical purity of 98%.

Characterisation of the product thereby formed, using the techniques given in Examples 4 to 5, demonstrated that the crystalline form I of the hydrochloride was obtained.

Example 4

Crystalline form I of 4-{3-[cis-hexahydrocyclopenta[c]pyrrol-2(1H)-yl]propoxy}benzamide hydrochloride Prior to recording the X-ray diffraction diagram, the samples obtained according to the procedure described in one of Examples 1 to 3 were milled for 30 seconds at 30 Hz in the presence of 100 μL of anhydrous ethanol per 200 mg of active ingredient in a 25-ml stainless-steel jar containing 2 stainless-steel balls.

Recording of the data was carried out using a PANalytical X'Pert Pro MPD diffractometer with an X'Celerator detector under the following conditions:
Voltage 45 kV, current 40 mA,
Mounting: theta/theta,
Anode: copper,
K alpha-1 wavelength: 1.54060 Å,
K alpha-2 wavelength: 1.54443 Å,
K alpha-2/K alpha-1 ratio: 0.5
Measurement mode: continuous from 3° to 55° (Bragg's angle 2 theta) in increments of 0.017°,
Measurement time per step: 35.53 s.

The X-ray powder diffraction diagram of form I of the 4-{3-[cis-hexahydrocyclopenta[c]pyrrol-2(1H)-yl]propoxy}benzamide hydrochloride thereby obtained is expressed in terms of line position (Bragg's angle 2 theta, expressed in degrees ±0.2°), interplanar distance (expressed in Å) and relative intensity (expressed as a percentage relative to the most intense line). The significant lines are collated in the following table:

| Line no. | Angle 2-theta (degrees) | Interplanar distance (Å) | Relative intensity (%) |
|---|---|---|---|
| 1 | 16.97 | 5.219 | 9.7 |
| 2 | 17.84 | 4.967 | 21.6 |
| 3 | 18.90 | 4.690 | 100 |
| 4 | 20.32 | 4.366 | 41.8 |
| 5 | 23.87 | 3.724 | 15.4 |
| 6 | 27.10 | 3.288 | 44.7 |
| 7 | 27.86 | 3.200 | 6.6 |
| 8 | 30.34 | 2.943 | 21.7 |

The following parameters were thereby determined:
monoclinic crystalline unit cell,
unit cell parameters: a=10.6621 Å, b=10.4945 Å, c=15.6542 Å, β=101.949°
space group: P 1 2$_1$/c 1 (14)
number of molecules in the unit cell: 4
volume of the unit cell: $V_{unit\ cell}$=1713.637 Å$^3$
density: d=1.2590 g/cm$^3$.

Example 5

Crystalline form I of 4-{3-[cis-hexahydrocyclopenta[c]pyrrol-2(1H)-yl]propoxy}benzamide hydrochloride Form I of 4-{3-[cis-hexahydrocyclopenta[c]pyrrol-2(1H)-yl]propoxy}benzamide hydrochloride was characterised by Raman spectroscopy. The spectra were recorded in reflection mode (PerkinElmer) and transmission mode (Cobalt) with laser focalisation of 785 nm and 830 nm respectively, using a CCD detector. The wavelength shift depends on the material and is characteristic of that material, which allows analysis of the chemical composition and of the molecular arrangement of the sample studied. The spectra are acquired:
in reflection mode with a laser power of 400 mW, a spot size of 100 μm, five exposures of five seconds and a spectral resolution of 2 cm$^{-1}$,
in transmission mode with a laser power of 650 mW, a spot size of 4 mm, twenty exposures of 3 seconds and a spectral resolution of 2 cm$^{-1}$.

The spectral range explored ranges from 0 to 3278 cm$^{-1}$ in reflection mode and from 37 to 2400 cm$^{-1}$ in transmission mode.

Significant peaks were observed at the following locations: 1676 cm$^{-1}$, 1606 cm$^{-1}$, 1564 cm$^{-1}$, 1152 cm$^{-1}$, 830 cm$^{-1}$ and 296 cm$^{-1}$.

Example 6

Crystalline form I of the free base of 4-{3-[cis-hexahydrocyclopenta[c]pyrrol-2(1H)-yl]propoxy}benzamide Recording of the data was carried out using a PANalytical X'Pert Pro MPD diffractometer with an X'Celerator detector under the following conditions:
Voltage 45 kV, current 40 mA,
Mounting: theta/theta,
Anode: copper,
K alpha-1 wavelength: 1.54060 Å,
K alpha-2 wavelength: 1.54443 Å,
K alpha-2/K alpha-1 ratio: 0.5
Measurement mode: continuous from 3° to 55° (Bragg's angle 2 theta) in increments of 0.017°,
Measurement time per step: 35.53 s.

The X-ray powder diffraction diagram of form I of the free base of 4-{3-[cis-hexahydrocyclopenta[c]pyrrol-2(1H)-yl]propoxy}benzamide obtained according to the process of one of Examples 1 to 3 is expressed in terms of line position (Bragg's angle 2 theta, expressed in degrees ±0.2°), interplanar distance (expressed in Å) and relative intensity (expressed as a percentage relative to the most intense line). The significant lines are collated in the following table:

| Line no. | Angle 2-theta (degrees) | Interplanar distance (Å) | Relative intensity (%) |
|---|---|---|---|
| 1 | 6.25 | 14.131 | 6.6 |
| 2 | 12.55 | 7.049 | 16.3 |
| 3 | 17.74 | 4.997 | 100 |
| 4 | 18.19 | 4.873 | 7.3 |
| 5 | 19.43 | 4.565 | 13.3 |
| 6 | 20.72 | 4.284 | 32.2 |
| 7 | 21.00 | 4.226 | 7.7 |
| 8 | 23.50 | 3.782 | 51.4 |
| 9 | 27.00 | 3.297 | 5.9 |

Example 7

Crystalline form I of the free base of 4-{3-[cis-hexahydrocyclopenta[c]pyrrol-2(1H)-yl]propoxy}benzamide Form I of the free base of 4-{3-[cis-hexahydrocyclopenta[c]pyrrol-2(1H)-yl]propoxy}benzamide was characterised by Raman spectroscopy. The spectra were recorded in transmission mode (Cobalt) with laser focalisation of 830 nm using a CCD detector. The wavelength shift depends on the material and is characteristic of that material, which allows analysis of the chemical composition and of the molecular arrangement of the sample studied. The spectra are acquired with a laser power of 650 mW, a spot size of 4 mm, twenty exposures of 0.9 second and a spectral resolution of 2 cm$^{-1}$. The spectral range explored ranges from 37 to 2400 cm$^{-1}$.

Significant peaks were observed at the following locations: 292 cm$^{-1}$, 618 cm$^{-1}$, 1045 cm$^{-1}$, 1483 cm$^{-1}$, 1568 cm$^{-1}$, 1683 cm$^{-1}$.

Example 8

Crystalline form I of the free base of 4-{3-[cis-hexahydrocyclopenta[c]pyrrol-2(1H)-yl]propoxy}benzamide Form I of the free base of 4-{3-[cis-hexahydrocyclopenta[c]pyrrol-2(1H)-yl]propoxy}benzamide was also characterised by solid-state NMR spectroscopy. The solid-state $^{13}$C NMR spectra were recorded at ambient temperature using a Bruker SB Avance spectrometer with a 4-mm CP/MAS SB VTN type probe under the following conditions:
  Frequency: 125.76 MHz,
  Spectral width: 40 kHz,
  Magic angle spinning rate: 13 kHz,
  Pulse program: Cross Polarization with SPINAL64 decoupling (decoupling power of 80 kHz),
  Recycle delay: 10 s,
  Acquisition time: 47 ms,
  Contact time: 4 ms,
  Number of scans: 4096.

The spectra thereby obtained were referenced relative to a sample of adamantane. The peaks observed are collated in the following table (expressed in ppm±0.2 ppm):

| Peak no. | Chemical shift (ppm) |
| --- | --- |
| 1 | 173.2 |
| 2 | 162.2 |
| 3 | 132.4 |
| 4 | 128.6 |
| 5 | 127.2 |
| 6 | 119.2 |
| 7 | 112.2 |
| 8 | 67.1 |
| 9 | 64.0 |
| 10 | 59.7 |
| 11 | 52.1 |
| 12 | 44.5 |
| 13 | 42.8 |
| 14 | 31.5 |
| 15 | 30.8 |
| 16 | 30.2 |
| 17 | 26.2 |

Example 9

Pharmaceutical Composition

Formula for the Preparation of 1000 Tablets Each Containing 5 mg of Active Ingredient (Expressed as Equivalent to the Base):
  Compound of Example 1 (expressed as equivalent to the base) . . . 5 g
  Maize starch . . . 20 g
  Maltodextrin . . . 7.5 g
  Colloidal silica . . . 0.2 g
  Sodium starch glycolate . . . 3 g
  Magnesium stearate . . . 1 g
  Lactose . . . 65 g

The invention claimed is:
1. A process for the synthesis of a compound of formula (I):

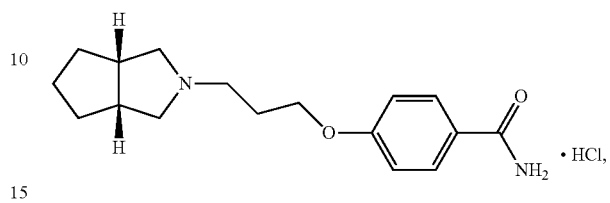

wherein a compound of formula (II):

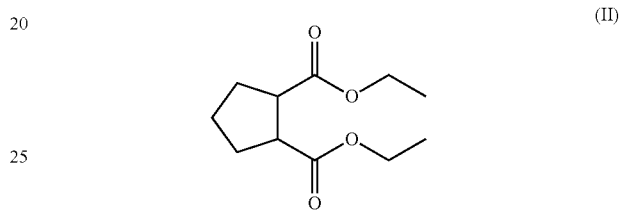

is reacted with ammonia at a temperature greater than 100° C. to form a compound of formula (III):

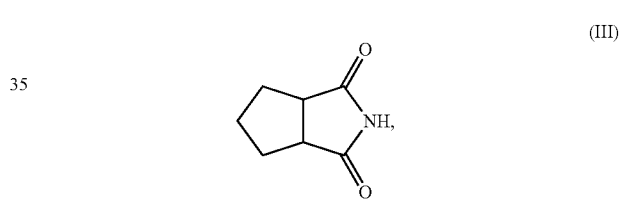

which is reduced to yield a bicyclic amine of formula (IV):

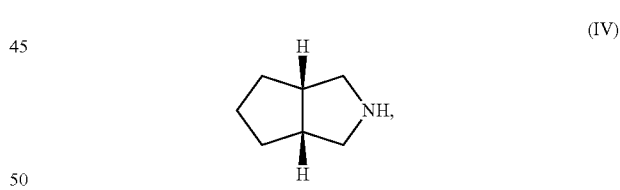

which latter compound is subsequently subjected:
  either to a coupling reaction, under basic conditions in a polar medium, with a compound of formula (V):

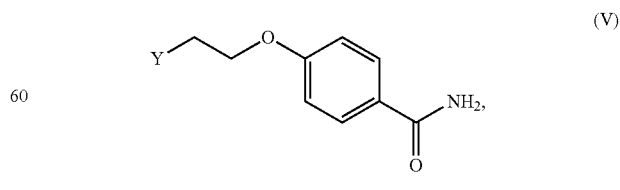

wherein Y represents —CH$_2$-Hal wherein Hal is a halogen, or a —CH$_2$—OSO$_2$—R group wherein R is an (C$_1$-C$_6$)alkyl group or a —C$_6$H$_4$—CH$_3$ group, or to reductive amination, in an acid medium, with a compound of formula (V'):

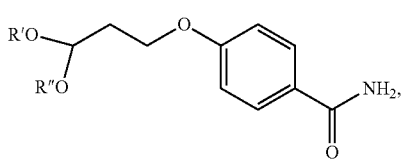

wherein R' and R" represent, each independently of the other, a (C$_1$-C$_6$)alkyl group, or R' and R" together form a group —(CH$_2$)$_n$— wherein n=2-3, or one of the groups R' and R" represents a hydrogen atom and the other represents a (C$_1$-C$_6$)alkyl group, or to reductive amination with a compound of formula (V"):

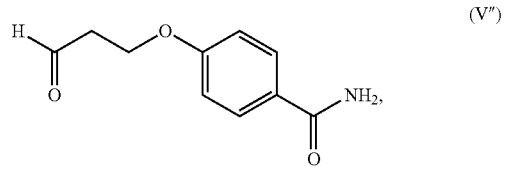 [SMILES: NC(=O)c1ccc(OCCC=O)cc1]

to yield the free base of the compound of formula (I), which is placed in the presence of HCl to form the compound of formula (I), which is isolated in the form of a solid.

2. The process according to claim 1, wherein the reaction mixture obtained at the end of the reaction of the compound of formula (II) with ammonia is subjected to pyrolysis.

3. The process according to claim 2, wherein the pyrolysis is carried out at a temperature greater than or equal to 200° C.

4. The process according to claim 2, wherein the pyrolysis is carried out at a temperature greater than or equal to 280° C.

5. The process according to claim 1, wherein the conversion of the compound of formula (III) into the compound of formula (IV) is carried out in the presence of hydrogen and a metal or metal-containing catalyst.

6. The process according to claim 1, wherein the compound of formula (V) is 4-(3-chloropropoxy)benzamide.

7. The process according to claim 1, wherein the coupling reaction of the compound of formula (IV) with the compound of formula (V) is carried out in the presence of a carbonate, an amine or a hydroxide.

8. The process according to claim 1, wherein the coupling reaction of the compound of formula (IV) with the compound of formula (V) is carried out in the presence of potassium carbonate or triethylamine.

9. The process according to claim 1, wherein the coupling reaction of the compound of formula (IV) with the compound of formula (V) is carried out in a polar medium composed of one or more polar solvents selected from water, alcohols, ketones, ethers, amides, DMSO and acetonitrile.

10. The process according to claim 1, wherein the coupling reaction of the compound of formula (IV) with the compound of formula (V) is carried out in a water/acetonitrile mixture or a water/isopropanol mixture.

11. The process according to claim 1, wherein the salt formation step in the presence of HCl takes place in a solvent selected from water, acetone and an alcohol.

12. The process according to claim 1, wherein the salt formation step in the presence of HCl takes place in acetone or isopropanol.

13. The process according to claim 1, wherein the compound of formula (I) is subjected to recrystallisation.

14. A compound of formula (V)

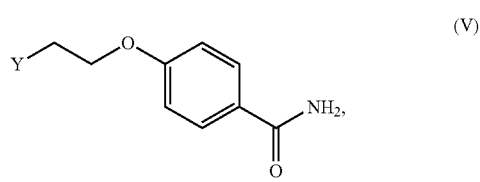

wherein Y represents a —CH$_2$—OSO$_2$—R group wherein R is an (C$_1$-C$_6$)alkyl group or a —C$_6$H$_4$—CH$_3$ group.

15. A compound of formula (V')

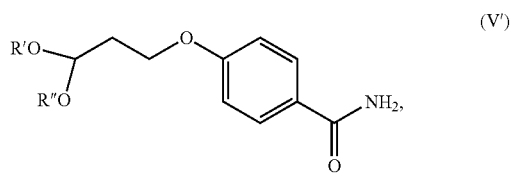

wherein R' and R" represent, each independently of the other, a (C$_1$-C$_6$)alkyl group, or R' and R" together form a group —(CH$_2$)$_n$— wherein n=2-3, or one of the groups R' and R" represents a hydrogen atom and the other represents a (C$_1$-C$_6$)alkyl group.

16. The compound according to claim 15 which is 4-(3,3-diethoxypropoxy)benzamide.

* * * * *